United States Patent [19]

Kozarsky et al.

[11] Patent Number: 5,558,835
[45] Date of Patent: Sep. 24, 1996

[54] LEAD TEST DAUBER

[75] Inventors: Eliot M. Kozarsky, Moorestown, N.J.; Dianne C. Horton, Terrell, N.C.

[73] Assignee: Universal Synergetics, Inc., Mt. Laurel, N.J.

[21] Appl. No.: 240,038

[22] Filed: May 9, 1994

[51] Int. Cl.$^6$ ............................. G01N 33/20; G01N 21/78
[52] U.S. Cl. ........................... 422/56; 422/58; 422/61; 436/73; 436/77; 436/84; 436/169; 451/523; 451/525; 15/118
[58] Field of Search ........................ 422/56–58, 61, 422/50; 436/77, 81, 84, 169, 79, 73; 451/461, 523, 525; 15/104.93, 104.94, 105, 118

[56] References Cited

U.S. PATENT DOCUMENTS

| | | | |
|---|---|---|---|
| 3,998,012 | 12/1976 | Ness | 51/391 |
| 4,004,376 | 1/1977 | Schepp et al. | 51/181 R |
| 4,724,568 | 2/1988 | Englehardt | 15/118 |
| 4,797,243 | 1/1989 | Wolbrom | 264/126 |
| 4,870,116 | 9/1989 | Wolbrom | 521/143 |
| 5,039,618 | 8/1991 | Stone | 436/77 |
| 5,278,075 | 1/1994 | Stone | 436/73 |
| 5,320,969 | 6/1994 | Bauer et al. | 436/84 |
| 5,330,917 | 7/1994 | Stone | 436/73 |
| 5,364,792 | 11/1994 | Stone | 436/73 |

*Primary Examiner*—Jeffrey Snay
*Assistant Examiner*—Harold Y. Pyon
*Attorney, Agent, or Firm*—Norman E. Lehrer; Jeffrey S. Ginsberg

[57] ABSTRACT

A device for testing for the presence of lead on a painted surface includes a porous dauber formed from an absorbent sintered plastic. The dauber is preimpregnated with a powdered mixture containing rhodizonate dye which is activated by dipping the dauber in a small quantity of water. After activation, the dauber is rubbed on the surface and is then visually observed for a reaction with lead that may be in the surface. The device also includes an abrasive element that can be used to abrade the painted surface before contacting the same with the dauber.

13 Claims, 1 Drawing Sheet

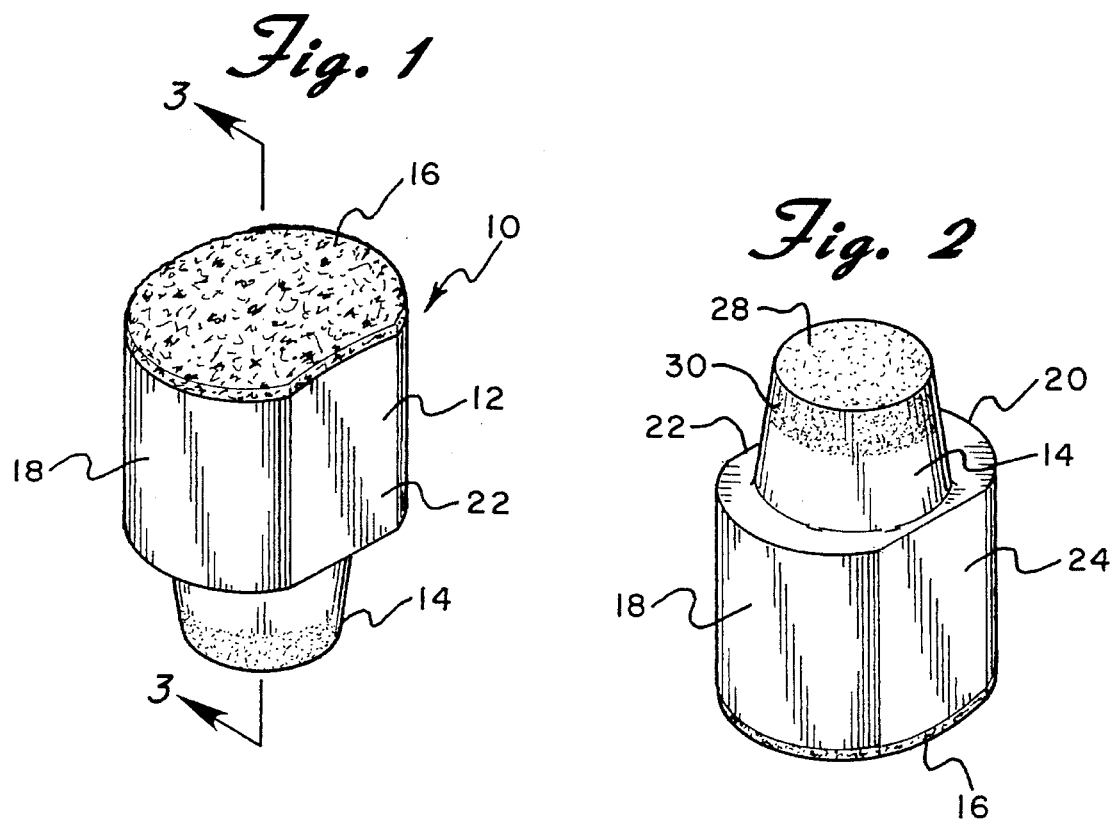
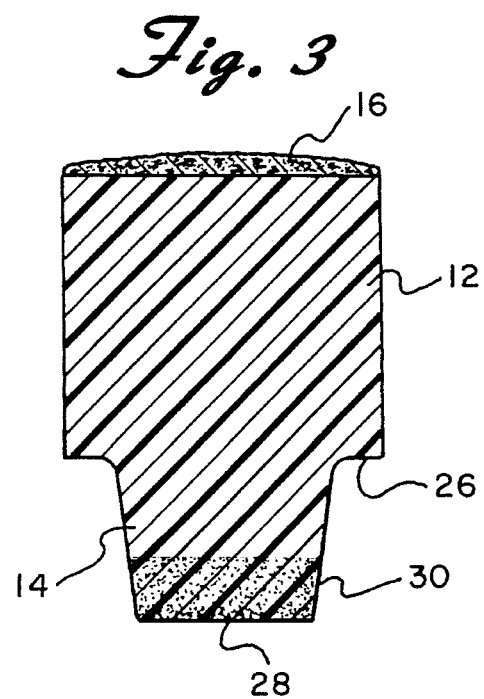

LEAD TEST DAUBER

BACKGROUND OF THE INVENTION

The present invention is directed toward a device for testing for the presence of a specific substance on a surface and, more particularly, toward a small, hand-held dauber which is preimpregnated with a dry powder which, when wetted and rubbed on a painted surface, will indicate the presence of lead in the paint by merely visually observing the dauber.

As is well known in the art, it was common practice at one time for paint manufacturers to incorporate lead in the paint in order to improve the characteristics thereof. When it became apparent, however, that paint chips were being ingested by small children causing brain damage and other defects caused by the lead, lead was banned as an additive for paints. Unfortunately, many homes and other buildings, particularly in the inner cities, continue to have paint on windowsills, frames and walls and the like which contain lead therein and this continues to cause a health hazard.

While many homeowners, landlords and government agencies have removed the lead-based paints from these older buildings, others have simply painted over the old paint with newer, safer paints. Although this provides some measure of protection, it provides no benefit to a small child who may be biting or teething on a windowsill and who may scratch through the top layer of paint to the lead-based paint below. Furthermore, should paint chip off of the painted surface, the paint chips would frequently be comprised of many layers of paint and would, therefore, include lead therein.

Numerous tests have been developed over the years for checking for the presence of lead in painted surfaces. The majority of these require that a paint chip or the like be removed and sent to a laboratory for analysis. Obviously, this is time consuming and, therefore, relatively expensive.

A more convenient, do-it-yourself type test has been developed and is available in the marketplace under the name Lead Check which is sold by Hybrivet Systems, Inc., of Framingham, Mass. This commercially available product includes a hollow, elongated tubular handle having a pair of breakable glass ampules therein. One of the ampules contains a dry powder containing a rhodizonate dye while the other contains an activating solution. An absorbent ball of material such as cotton, felt or the like is mounted at the end of the elongated cylindrical handle. When it is desired to utilize the device, the handle is squeezed or otherwise flexed so as to break the ampules therein. The contents of the ampules mix and are absorbed by the swab ball. The swab can then be rubbed on the painted surface and the presence of lead will be indicated by a red color that appears on the swab. This prior art device is described in U.S. Pat. No. 5,039,618 to Stone.

The Hybrivet test swab has proven to be somewhat useful. However, it is relatively expensive since the ampules must be prepared separately and along with the various other component parts must be assembled to form the finished device. Furthermore, the Hybrivet device can only test for lead on the outermost surface of the paint. Since the device is incapable of scratching beneath the outer surface, it cannot test for lead in an underlayer of paint. There is, therefore, a need for an inexpensive, do-it-yourself type lead tester which is easy to use and which can test for lead beneath the outer surface of the paint.

SUMMARY OF THE INVENTION

The present invention overcomes the deficiencies of the prior art discussed above and provides a simple and inexpensive do-it-yourself tester for testing for the presence of lead on a painted surface. The device includes a porous dauber formed from an absorbent sintered plastic. The dauber is preimpregnated with a powdered mixture containing rhodizonate dye which is activated by dipping the dauber in a small quantity of water. After activation, the dauber is rubbed on the surface and is then visually observed for a reaction with lead that may be in the surface. The device also includes an abrasive element that can be used to abrade the painted surface before contacting the same with the dauber.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a perspective view of a lead test dauber constructed in accordance with the principles of the present invention;

FIG. 2 is an inverted perspective view of the device shown in FIG. 1, and

FIG. 3 is a cross-sectional view taken through the line 3—3 of FIG. 1.

DETAILED DESCRIPTION OF THE PREFERRED EMBODIMENT

Referring now to the drawings in detail wherein like reference numerals have been used throughout the various figures to designate like elements, there is shown in FIG. 1 a perspective view of a lead test dauber constructed in accordance with the principles of the present invention and designated generally as 10. The lead test dauber 10 is comprised essentially of three principal parts: a central handle portion 12, a lower dauber portion 14 and an upper abrading portion 16.

As is shown most clearly in FIGS. 1 and 2, the central handle portion 12 includes two opposed and vertically extending curved walls 18 and 20 and two vertically extending flat walls 22 and 24 interposed between the walls 18 and 20. The handle portion 12 is preferably approximately ½ inch high, ¾ inch along its long axis and ½ inch along its shorter axis. It is, essentially, of such a size and configuration so as to be easily held with the tips of a person's thumb and forefingers. The handle portion 12 is preferably comprised of a nonabsorbent, molded plastic material.

Mounted on the top surface of the upper end of the handle portion 12 is the abrasive portion 16. The abrasive portion 16 is comprised of a layer of particulate abrasive material such as silicon dioxide or the like contained within a base and can be either separately prepared and adhered to the top of the handle portion 12 or can be molded thereon.

Secured to the lower surface 26 of the lower end of the handle portion 12 is a dauber element 14. The dauber element 14 is preferably of an inverted frusto-conical shape having a planar lower surface 28. It is of substantially circular cross section having a diameter of approximately ⅜ inch and an overall height of approximately ⅜ inch.

The dauber element 14 is a substantially rigid but liquid absorbent plastic and is preferably formed of a light-colored sintered plastic material. The manner in which the dauber element 14 is formed is described in U.S. Pat. Nos. 4,797,243 and 4,870,116 to Wolbrom. In one form of the invention, it may be preferable to have only the bottom half 30 or the bottom third of the dauber portion 14 be absorbent and the remaining portion be hydrophobic similar to the handle portion 12.

Although the handle portion 12 is preferably made of a non-liquid absorbent plastic material while the dauber element 14 is absorbent, it is also possible to make the entire device of an absorbent sintered plastic material and to include a liquid barrier between the handle portion 12 and the dauber element 14 or between the bottom and top halves of the dauber element 14. In any case, the entire device can be molded so as to co-join all three of the primary components thereof.

Embedded within and substantially evenly distributed throughout the lower portion 26 of dauber element 14 is a dry powdered reagent material utilized to test for the presence of lead. The reagent material is comprised essentially of rhodizonate, an inert filler and a buffer. In the preferred embodiment of the invention, the dry powder reagent material includes approximately 2.5 milligrams of aluminum oxide filler material, 0.4 milligrams of a dye comprised of a sodium salt of rhodizonic acid and a buffer comprised of 13.6 milligrams of potassium bitartrate and 1 milligram of tartaric acid. Approximately 5 to 20 milligrams of this reagent powder is combined with approximately 40 milligrams of the sintered plastic material forming the lower part porous dauber element 14. The manner in which the dry powdered reagent material is combined with and impregnated into the porous, sintered plastic material forming the dauber element 14 so as to form a porous dauber is also described in the two Wolbrom patents referred to above.

As is well known in the art, an aqueous solution including the rhodizonate dye is unstable and completely degrades in a relatively short period of time. It is, for this reason, that the dauber element 14 of the present invention includes the dye therein in a dry powdered form and as long as it remains dry, it has an extremely long shelf life.

The lead testing device 10 of the present invention is utilized in the following manner. It is first inverted so as to be in the position shown in FIG. 2. The dauber element 14 and handle portion 12 can then be easily grasped with a person's thumb and fingertips and the surface to be tested is abraded by rubbing the abrasive material 16 thereon so as to scratch the surface. This initial process removes the upper layer or layers of paint and exposes older paint that may be one or two or several layers beneath the upper surface depending on how much abrasive action is used. The device is then re-inverted to its initial form as shown in FIGS. 1 and 3 and the porous tip 26 of dauber element 14 is dipped in a small quantity (approximately 1 cc) of water. The water mixes with the dry powdered dye reagent within the dauber 14 creating a reagent solution. The lower surface 28 of the dauber element 14 is then rubbed on the abraded painted surface for a few seconds. Thereafter, the tip 28 of the dauber element 14 is visually inspected. A red or pink color indicates the presence of lead in the painted surface.

In some circumstances and depending on the color of the sintered plastic material, it may be necessary to add a white pigment to the bottom portion 26 of the dauber. This will provide a better contrast so that it will be more readily apparent as to whether a pink or red color is present.

The present invention may be embodied in other specific forms without departing from the spirit or essential attributes thereof. For example, while the device is described as being useful for the detection of lead, other reagents can be used to test for other substances. Other shapes and materials for the device are also possible. Accordingly, reference should be made to the appended claims rather than to the foregoing specification as indicating the scope of the invention.

I claim:

1. A device for testing for a substance in a surface with a reagent material that is capable of reacting with the substance comprising:

a handle portion adapted to be held by a person utilizing the device, said handle portion having an upper end and a lower end;

a substantially rigid but liquid absorbent dauber secured to the lower end of said handle portion, at least a component of said reagent material impregnated within said dauber;

abrasive means carried adjacent the upper end of said handle portion for abrading said surface prior to testing; and wherein said abrasive means is comprised of a layer of the particulate abrasive material mounted on the upper end of said handle portion.

2. The device as claimed in claim 1 wherein the substance tested for is lead.

3. The device as claimed in claim 2 wherein said reagent material includes rhodizonate.

4. The device as claimed in claim 1 wherein said reagent material is in dry powder form within said dauber.

5. The device as claimed in claim 4 wherein said absorbent dauber is capable of being wetted with water to form a reagent solution within said dauber.

6. The device as claimed in claim 1 wherein said handle portion is larger in diameter than said dauber.

7. The device as claimed in claim 1 wherein said dauber is comprised of absorbent plastic.

8. The device as claimed in claim 7 wherein said dauber is formed of sintered plastic.

9. The device as claimed in claim 1 wherein said handle portion is non-absorbent.

10. The device as claimed in claim 1 wherein said dauber and said handle portion are formed of sintered plastic with said dauber being absorbent and said handle portion being non-absorbent.

11. In a device for testing for a substance on a surface wherein said device includes an absorbent portion having a reagent therein adapted to contact said surface, the improvement comprising an abrasive means carried by said device for abrading said surface prior to contacting the surface with said absorbent portion, wherein said device includes a handle portion, wherein said abrasive means is carried by said handle portion, wherein said handle portion has two ends, said absorbent portion being mounted adjacent one end and said abrasive means being mounted adjacent the other end of said handle portion, and wherein said abrasive means is comprised of a layer of the particulate abrasive material mounted on the remote other end of said handle portion.

12. The device as claimed in claim 11 wherein said reagent reacts with lead to give a visual indication of the presence of lead in said surface.

13. The device as claimed in claim 11 wherein said handle portion and said absorbent portion are both comprised of sintered plastic, said handle portion being non-absorbent.

* * * * *